US010537555B2

United States Patent
Wang et al.

(10) Patent No.: US 10,537,555 B2
(45) Date of Patent: Jan. 21, 2020

(54) COMPLEX OF ANGIOTENSIN RECEPTOR ANTAGONIST AND NEUTRAL ENDOPEPTIDASE INHIBITOR

(71) Applicant: CHENGDU EASTON BIOPHARMACEUTICALS CO., LTD., Chengdu (CN)

(72) Inventors: Ying Wang, Chengdu (CN); Long Huang, Chengdu (CN); Yongzhe Xiang, Chengdu (CN); Guodong Cen, Chengdu (CN); Jianguo Li, Chengdu (CN); Jianjing Jia, Chengdu (CN); Qiangqiang Liu, Chengdu (CN); Yang Liu, Chengdu (CN); Haitao Yang, Chengdu (CN); Qing Dong, Morris Plains, NJ (US)

(73) Assignee: Chengdu Easton Biopharmaceuticals Co., Ltd, Chengdu (CN)

( * ) Notice: Subject to any disclaimer, the term of this patent is extended or adjusted under 35 U.S.C. 154(b) by 0 days.

(21) Appl. No.: 15/764,244

(22) PCT Filed: Sep. 1, 2016

(86) PCT No.: PCT/CN2016/097751
§ 371 (c)(1),
(2) Date: Mar. 28, 2018

(87) PCT Pub. No.: WO2017/080290
PCT Pub. Date: May 18, 2017

(65) Prior Publication Data
US 2018/0318259 A1   Nov. 8, 2018

(30) Foreign Application Priority Data

Nov. 9, 2015 (CN) .......................... 2015 1 0758232

(51) Int. Cl.
| C07D 257/04 | (2006.01) |
| A61K 31/41 | (2006.01) |
| A61P 9/04 | (2006.01) |

(52) U.S. Cl.
CPC ............ *A61K 31/41* (2013.01); *A61P 9/04* (2018.01); *C07D 257/04* (2013.01)

(58) Field of Classification Search
CPC .................................................. C07D 257/04
See application file for complete search history.

(56) References Cited

U.S. PATENT DOCUMENTS

| 2009/0149521 A1 | 6/2009 | Choi |
| 2009/0156585 A1 | 6/2009 | Feng |
| 2010/0267786 A1 | 10/2010 | Al-Fayoumi |

FOREIGN PATENT DOCUMENTS

| CN | 1972679 A | 5/2007 |
| CN | 101848700 A | 9/2010 |
| CN | 101896470 A | 11/2010 |
| CN | 102702119 A | 10/2012 |
| CN | 105669581 A | 6/2016 |
| WO | WO 2006/000564 A1 | 1/2006 |
| WO | WO 2007/056546 A1 | 5/2007 |
| WO | WO 2009/061713 A1 | 5/2009 |

OTHER PUBLICATIONS

Chemical Abstracts Registry No. 936623-90-4, indexed in the Registry file on STN CAS Online on Jun. 6, 2007 (Year: 2007).*
State Intellectual Property Office of the People's Republic of China, International Search Report and Written Opinion in corresponding International Application No. PCT/CN2016/097751, dated Dec. 5, 2016 (14 pages).
EP 16863468.1 Extended European Search Report dated Aug. 29, 2018, 8 pages.

* cited by examiner

*Primary Examiner* — Laura L Stockton
(74) *Attorney, Agent, or Firm* — Nixon Peabody LLP (57) ABSTRACT

Provided a complex of formula is [3-((1S, 3R)-1-biphenyl-4-ylmethyl-3-ethoxycarbonyl-1-butylcarbamoyl) propionate-(S)-3'-methyl-2'-(pentanoyl {2"-(tetrazol-5-ylate) biphenyl-4'-ylmethyl}amino) butyrate]$_6$.XCa$^{2+}$.YNa$^+$ .ZH$_2$O, wherein X=1-3, Y=12-16, Z=9-18, and 2X+Y=18, and represented by formula (I). Also disclosed are the method of preparing the complex and the method of treating chronic heart disease using a medicament comprising the complex.

19 Claims, 3 Drawing Sheets

COMPLEX OF ANGIOTENSIN RECEPTOR ANTAGONIST AND NEUTRAL ENDOPEPTIDASE INHIBITOR

CROSS-REFERENCE TO RELATED APPLICATIONS

This application is a U.S. national stage of PCT/CN2016/097751, filed on Sep. 1, 2016, which claims priority to Chinese Patent Application No. 201510758232.8 filed on Nov. 9, 2015.

TECHNICAL FIELD

The present invention relates to a complex comprising an angiotensin receptor blocker (ARB) and a neutral endopeptidase inhibitor (NEPi), in particular to a [3-((1S, 3R)-1-biphenyl-4-ylmethyl-3-ethoxycarbonyl-1-butylcarbamoyl)propionate-(S)-3'-methyl-2'-(pentanoyl {2"-(tetrazol-5-ylate)biphenyl-4'-ylmethyl}amino)butyrate] sodium calcium complex, as well as its methods of preparation and its applications in treating chronic heart failures.

BACKGROUND

Clinical manifestations of heart failure include shortness of breath, fatigue, and fluid retention (pulmonary congestion and peripheral edema). Patients suffering from heart failure need daily monitoring of the body weight to detect fluid retention so that adjustments to lifestyle and restrictions on sodium and fluid intake can be implemented as early as possible. Reducing sodium intake helps to reduce blood volume, water and sodium in the body, and to reduce blood pressure, which relieves the symptoms of heart failure.

Chronic heart failure is a heart dysfunction that is mainly due to pump dysfunction caused by the progressive decline in ventricular myocyte contractility. In the course of chronic heart failure, myocardial calcium homeostasis is damaged, manifested as decreases in the rise of intracellular calcium transient and its slower decay. This change is considered to be the main cause for impairment of myocardial contractility. Therefore, increasing calcium intake may alleviate blood pressure and sodium retention while maintaining normal myocardial contractility. In addition, the calcium ion is essential for a variety of physiological activities in the body, e.g., the biological potential on both sides of the cell membrane, normal nerve conductivity, and normal muscle contraction and relaxation.

LCZ696 (Entresto) is an angiotensin receptor neprilysin inhibitors (ARNi) that was developed by Novartis, which received FDA approval in July 2015. It treats chronic heart failure patients having reduced ejection fractions and can reduce death and hospitalization due to heart failure. LCZ696 is a complex containing anionic forms of sacubitril (AHU-377) and valsartan at a 1:1 ratio, sodium cations, as well as water molecules. Chinese Patent No. CN 200680001733.0 covers the complex and its crystalline forms.

LCZ696 is highly hygroscopic. It is found that, after ten days under high humidity conditions, LCZ696 absorbs water and turns into a liquid form. It is well known that hygroscopicity causes difficulties in granulations, disintegration, dissolution of the solid form during the formulation process, affecting the stability and efficacy of the drug product. Hygroscopic compounds also require more expensive and complex excipients, manufacturing processes, and storage facilities. Therefore, it is desirable to obtain a compound that is low in hygroscopy, more stable, and overall more effective.

SUMMARY OF THE INVENTION

The inventors of the application conducted a large amounts of experiments in an effort to find alternative salt forms to the complex containing [3-((1S, 3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate]. For example, potassium salts of the complex were investigated but only the potassium salt of valsartan was obtained. Complexes that contain both potassium and sodium cations were investigated. However, the resulting complexes have a sodium content similar to that of LCZ696, and no potassium was detected, indicating that they did not simultaneously contain sodium and potassium.

Organic bases, such as ammonium, triethanolamine, and piperazine, etc., have also be used to achieve a co-crystal complex with [3-((1S, 3R)-1-biphenyl-4-ylmethyl-3-ethoxycarbonyl-1-butylcarbamoyl) propionate-(S)-3'-methyl-2'-(pentanoyl {2"-(tetrazol-5-ylate)biphenyl-4'-ylmethyl}amino)butyrate], but failed to form crystalline structures. Furthermore, calcium salts of [3-((1S, 3R)-1-biphenyl-4-ylmethyl-3-ethoxycarbonyl-1-butylcarbamoyl) propionate-(S)-3'-methyl-2'-(pentanoyl {2"-(tetrazol-5-ylate)biphenyl-4'-ylmethyl}amino)butyrate] were also investigated but no complex was formed. Nevertheless, it was unexpectedly discovered that such calcium salt can be dissolved in acetone.

After extensive screening involving cations of calcium and other metals, stable complexes that contain [3-((1S, 3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] as well as sodium and calcium cations were obtained. Their XRPD patterns having characteristic peaks were exhibited in some embodiments, which indicated their formation of co-crystals featured with highly stable and controllable compositions.

The complex of one embodiment can be expressed as [3-((1S, 3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino) butyrate]$_6$.XCa$^{2+}$.YNa$^+$.ZH$_2$O, wherein X=1-3, Y=12-16, Z=9-18, and 2X+Y=18, while X, Y, and Z are preferably integers. In this disclosure, when in formula of the complex wherein X and/or Y are numbers, X and/or Y are written as subscripts while the valance numbers for Ca and Na are omitted to improve readability. The structure of the aforementioned complex is shown as below.

In some embodiments, X=1, Y=16, and Z=9-18. In other embodiments, X=1, Y=16, and Z=12-18. In still further embodiments, X=1, Y=16, and Z=12, 15, or 18. In one preferred embodiment, when X=1 and Y=16, Z=15.

Further embodiments described complexes in which X=2, Y=14, Z=9-18; X=2, Y=14, Z=9-15; or preferably when X=2, Y=14, Z=12, 15, or 9. In one preferred embodiment, X=2, Y=14, and Z=15.

Still further embodiments described complexes in which X=3, Y=12, Z=9-18; X=3, Y=12, Z=9-15; preferably when X=3 and Y=12, Z=12, 9, or 15. In one preferred embodiment, X=3, Y=12, Z=15.

Some specific embodiments also described complexes in which X=1, Y=16, Z=9; X=1, Y=16, Z=12; X=1, Y=16, Z=15; X=1, Y=16, Z=18; preferably when X=1 and Y=16, Z=12, 15 or 18; and X=2, Y=14, Z=18; X=2, Y=14, Z=15; or X=2, Y=14, Z=12; X=2, Y=14, Z=9; preferably when X=2 and Y=14, Z=9, 12 or 15; and X=3, Y=12, Z=18; or X=3, Y=12, Z=15; or X=3, Y=12, Z=12; or X=3, Y=12, Z=9; preferably when X=3 and Y=12, Z=9, 12, or 15.

The above-listed complexes are preferably in crystalline forms.

Complex I is [3-((1S, 3R)-1-biphenyl-4-ylmethyl-3-ethoxycarbonyl-1-butylcarbamoyl)propionate-(S)-3'-methyl-2'-(pentanoyl {2"-(tetrazol-5-ylate)biphenyl-4'-ylmethyl}amino) butyrate]$_6$·XCa$^{2+}$·YNa$^+$·ZH$_2$O, where in X=1, Y=16, and Z=15. Preferably this complex is in a crystalline form. Cu Kα X-ray powder diffraction (XRPD) was used to characterize Complex I. The diffraction angles, d-spacing, and relative intensity of peaks in the XRPD pattern of Complex I are shown in Table I.

TABLE I

| Peak No. | Pos. [°2θ]* | d-spacing [Å] | Rel. Int. [%] |
|---|---|---|---|
| 1 | 4.12 | 21.43 | 100.00 |
| 2 | 5.11 | 17.29 | 32.58 |

TABLE I-continued

| Peak No. | Pos. [°2θ]* | d-spacing [Å] | Rel. Int. [%] |
|---|---|---|---|
| 3 | 5.57 | 15.87 | 15.90 |
| 4 | 12.43 | 7.12 | 27.08 |
| 5 | 15.20 | 5.83 | 5.96 |
| 6 | 16.89 | 5.25 | 10.46 |
| 7 | 17.71 | 5.00 | 7.13 |
| 8 | 18.62 | 4.77 | 7.27 |
| 9 | 19.96 | 4.45 | 6.50 |

*The diffraction angle 2θ has a margin of error of ±0.2.

In further embodiments, the XRPD pattern of Complex I has diffraction angles, d-spacing, and relative intensity of peaks shown in Table II.

TABLE II

| Peak No. | Pos. [°2θ]* | d-spacing [Å] | Rel. Int. [%] |
|---|---|---|---|
| 1 | 4.12 | 21.43 | 100.00 |
| 2 | 5.11 | 17.29 | 32.58 |
| 3 | 5.57 | 15.87 | 15.90 |
| 4 | 8.72 | 10.14 | 1.29 |
| 5 | 10.20 | 8.67 | 2.04 |
| 6 | 12.43 | 7.12 | 27.08 |
| 7 | 13.26 | 6.68 | 2.55 |
| 8 | 15.20 | 5.83 | 5.96 |
| 9 | 16.89 | 5.25 | 10.46 |
| 10 | 17.71 | 5.00 | 7.13 |
| 11 | 18.62 | 4.77 | 7.27 |
| 12 | 19.96 | 4.45 | 6.50 |
| 13 | 22.48 | 3.96 | 4.09 |
| 14 | 24.89 | 3.58 | 2.88 |
| 15 | 26.92 | 3.31 | 2.05 |
| 16 | 28.97 | 3.08 | 1.57 |
| 17 | 33.09 | 2.71 | 0.63 |

*The diffraction angle 2θ has a margin of error of ±0.2.

Figure 1:
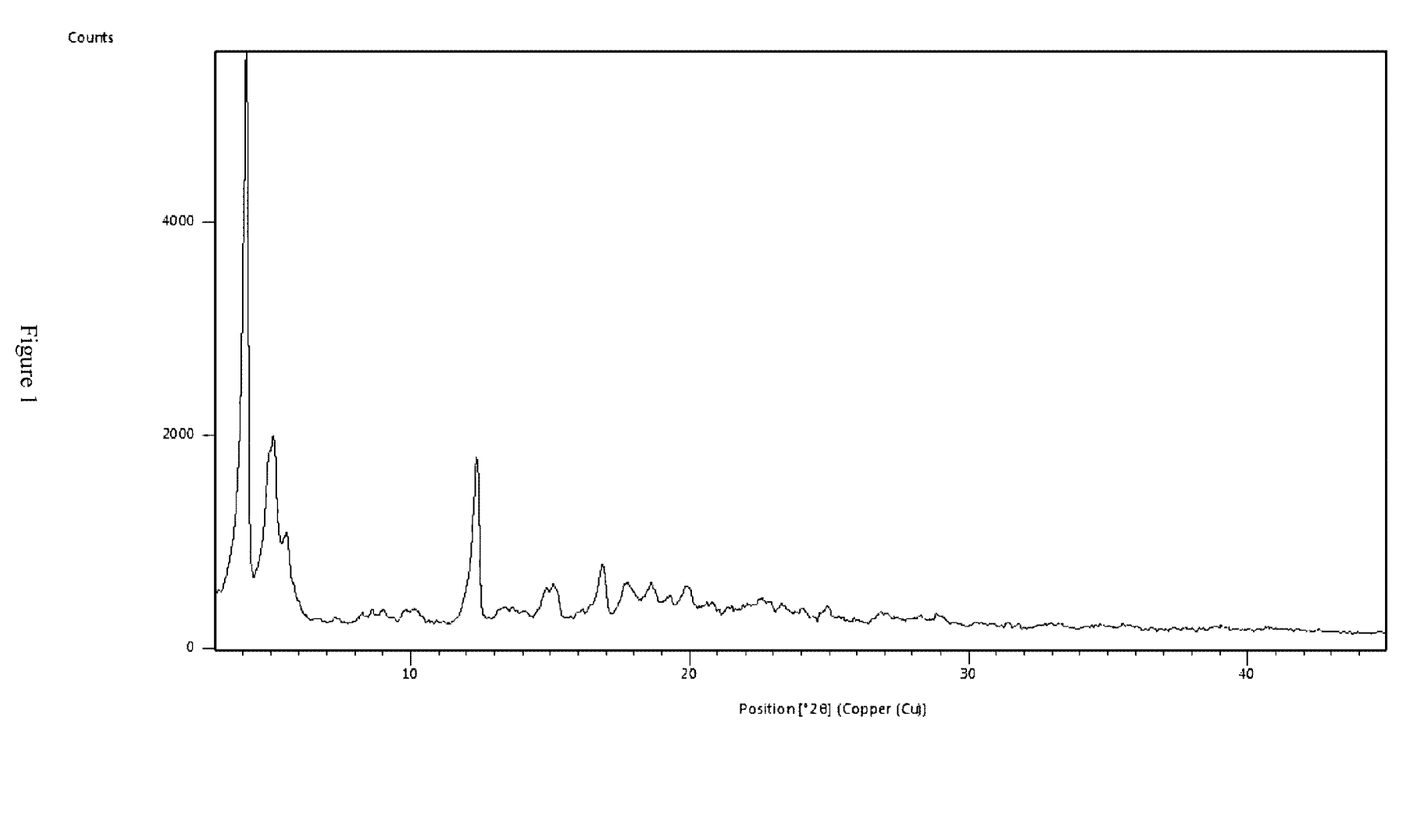
FIG. 1 is the X-ray diffraction pattern of Complex I.

In still further embodiments, Complex I has an XRPD pattern substantially as shown in FIG. 1.

Complex II is [3-((1S, 3R)-1-biphenyl-4-ylmethyl-3-ethoxycarbonyl-1-butylcarbamoyl)propionate-(S)-3'-methyl-2'-(pentanoyl {2"-(tetrazol-5-ylate)biphenyl-4'-ylmethyl}amino) butyrate]$_6$·XCa$^{2+}$·YNa$^+$·ZH$_2$O, where in X=2, Y=14, and Z=15. Preferably this complex is in a crystalline form. Cu Kα X-ray powder diffraction (XRPD) was used to characterize Complex II.

The XRPD pattern of Complex II has diffraction angles, d-spacing, and relative intensity of peaks shown in Table III.

TABLE III

| Peak No. | Pos. [°2θ]* | d-spacing [Å] | Rel. Int. [%] |
|---|---|---|---|
| 1 | 4.05 | 21.81 | 100.00 |
| 2 | 5.07 | 17.42 | 30.51 |
| 3 | 5.54 | 15.94 | 13.11 |
| 4 | 9.91 | 8.93 | 1.85 |
| 5 | 12.31 | 7.19 | 27.24 |
| 6 | 15.03 | 5.89 | 4.51 |
| 7 | 16.85 | 5.26 | 6.57 |
| 8 | 17.81 | 4.98 | 4.33 |
| 9 | 19.85 | 4.47 | 2.94 |

*The diffraction angle 2θ has a margin of error of ±0.2.

Furthermore, the crystalline form of Complex II has diffraction angles, d-spacing and relative intensity shown in the following Table IV.

TABLE IV

| Peak No. | Pos. [°2θ]* | d-spacing [Å] | Rel. Int. [%] |
|---|---|---|---|
| 1 | 4.05 | 21.81 | 100.00 |
| 2 | 5.07 | 17.42 | 30.51 |
| 3 | 5.54 | 15.94 | 13.11 |
| 4 | 8.60 | 10.29 | 1.30 |
| 5 | 9.91 | 8.93 | 1.85 |
| 6 | 12.31 | 7.19 | 27.24 |
| 7 | 13.50 | 6.56 | 1.32 |
| 8 | 15.03 | 5.89 | 4.51 |
| 9 | 16.85 | 5.26 | 6.57 |
| 10 | 17.81 | 4.98 | 4.33 |
| 11 | 19.85 | 4.47 | 2.94 |
| 12 | 22.88 | 3.89 | 1.54 |

*The diffraction angle 2θ has a margin of error of ±0.2.

Figure 2:
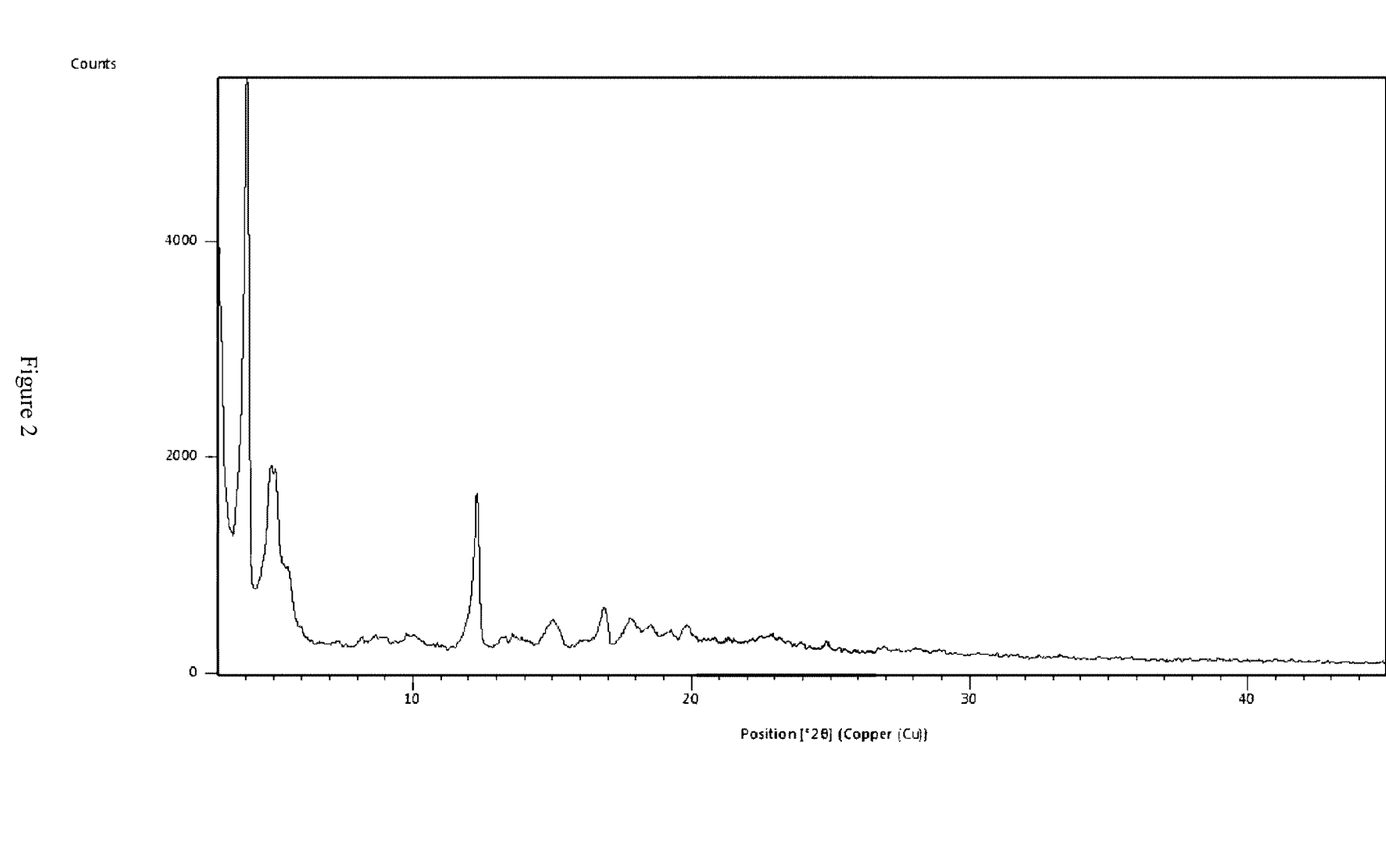
FIG. 2 is the X-ray diffraction pattern of Complex II.

In still further embodiments, Complex II has an XRPD pattern substantially as shown in FIG. 2.

Complex III is [3-((1S, 3R)-1-biphenyl-4-ylmethyl-3-ethoxycarbonyl-1-butylcarbamoyl) propionate-(S)-3'-methyl-2'-(pentanoyl{2"-(tetrazol-5-ylate) biphenyl-4'-ylmethyl}amino)butyrate]$_6$.XCa$^{2+}$.YNa$^+$.ZH$_2$O, wherein X=3, Y=12, Z=15. Preferably this complex is in a crystalline form. Cu Kα X-ray powder diffraction (XRPD) was used to characterize Complex III. The XRPD pattern of Complex III has diffraction angles, d-spacing, and relative intensity of peaks shown in Table V.

TABLE V

| Peak No. | Pos. [°2θ]* | d-spacing [Å] | Rel. Int. [%] |
|---|---|---|---|
| 1 | 4.06 | 21.78 | 100.00 |
| 2 | 5.03 | 17.39 | 60.81 |
| 3 | 5.52 | 16.02 | 26.11 |
| 4 | 8.59 | 10.29 | 5.01 |
| 5 | 9.81 | 9.01 | 4.08 |
| 6 | 12.33 | 7.18 | 24.95 |
| 7 | 15.22 | 5.82 | 7.45 |
| 8 | 16.87 | 5.26 | 11.75 |
| 9 | 17.83 | 4.97 | 7.78 |

*The diffraction angle 2θ has a margin of error of ±0.2.

Furthermore, the crystalline form of Complex III has a diffraction angle, spacing and relative intensity shown in the following Table VI.

TABLE VI

| Peak No. | Pos. [°2θ]* | d-spacing [Å] | Rel. Int. [%] |
|---|---|---|---|
| 1 | 4.06 | 21.78 | 100.00 |
| 2 | 5.03 | 17.39 | 60.81 |
| 3 | 5.52 | 16.02 | 26.11 |
| 4 | 8.59 | 10.29 | 5.01 |
| 5 | 9.81 | 9.01 | 4.08 |
| 6 | 12.33 | 7.18 | 24.95 |
| 7 | 13.48 | 6.57 | 2.97 |
| 8 | 15.22 | 5.82 | 7.45 |
| 9 | 16.87 | 5.26 | 11.75 |
| 10 | 17.83 | 4.97 | 7.78 |
| 11 | 22.81 | 3.90 | 3.26 |

*The diffraction angle 2θ has a margin of error of ±0.2.

Figure 3:
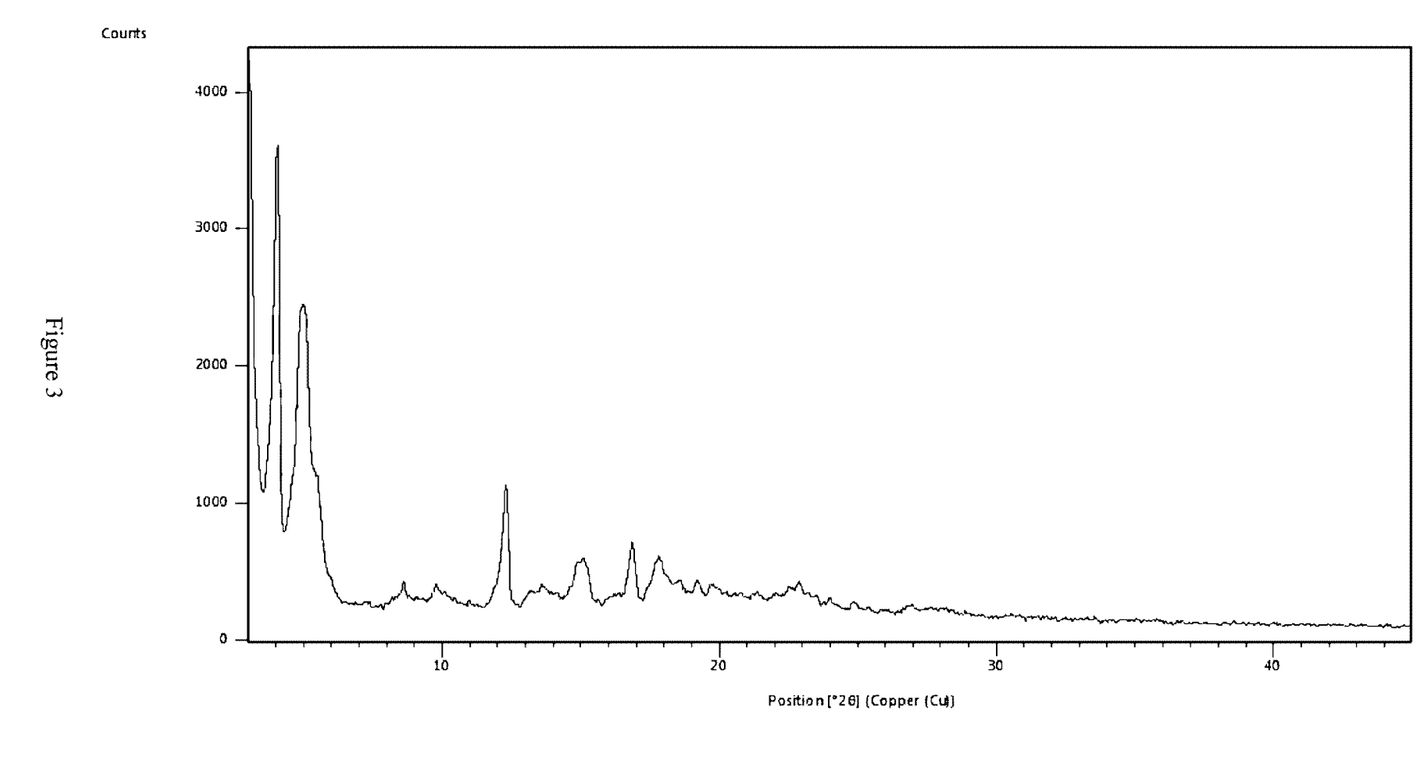
FIG. 3 is the X-ray diffraction pattern of Complex III.

In still further embodiments, Complex III has an XRPD pattern substantially as shown in FIG. 3.

The current disclosure also provides methods of preparation for complexes expressed as [3-((1S, 3R)-1-biphenyl-4-ylmethyl-3-ethoxycarbonyl-1-butylcarbamoyl)propionate-(S)-3'-methyl-2'-(pentanoyl {2"-(tetrazol-5-ylate)biphenyl-4'-ylmethyl} amino) butyrate]$_6$.XCa$^{2+}$.YNa$^+$.ZH$_2$O, wherein X=1-3, Y=12-16, Z=9-18, and 2X+Y=18. Such a preparation method includes the following steps: (1) adding calcium salts of AHU-377 and AHU-377 in acetone and stirring for 30 min until the salts completely dissolve to form a first solution; (2) adding valsartan or sodium salt of valsartan into the first solution, stirring until valsartan or valsartan salt completely dissolve to form a second solution; adding an aqueous NaOH solution into the second solution in 5 minutes, keep stirring at a constant speed, solids start to precipitate within about 20-30 minutes; (3) stirring for more than 6 hours, filtering the solution to obtain the solids, washing the solid filtrate three times with acetone, drying the solids at room temperature in ambient air.

Different Ca$^{2+}$:Na$^+$ molar ratios were chosen to form the complexes of the invention with different X and Y, e.g., Ca$^{2+}$:Na$^+$ molar ratios could be 1:16, 2:14, 3:12, 4:10, 5:8 or 6:6. It was discovered that at Ca$^{2+}$:Na$^+$ molar ratios of 1:16, 2:14, and 3:12, the crystalline form of the complex was stable in both its physical appearance and its chemical composition. The results were repeatable. On the other hand, when Ca$^{2+}$:Na$^+$ molar ratios was 4:10, 5:8, or 6:6, the complex was unstable. It was discovered that when making complexes with a Ca$^{2+}$:Na$^+$ molar ratio exceeding 3:12, additional calcium needs to be introduced through adding a calcium salt of Valsartan or adding calcium hydroxide, which could not dissolve completely in acetone. The resulting complexes are less suitable for making medicaments.

The current disclosure further provides a method of treating chronic heart failure using medications comprising a complex [3-((1S, 3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino) butyrate]$_6$.XCa$^{2+}$.YNa$^+$.ZH$_2$O, wherein X=1-3, Y=12-16, Z=9-18, and 2X+Y=18.

The complex disclosed therein has the following advantages:

1. The quality of the sample complexes prepared according to the method disclosed herein are stable and easily controllable. The sample have good chemical stability. Its solubility is similar to the comparative sample but significantly less hydroscopic. Its process of making and storage do not require special conditions, which leads to better efficacy and stability.

2. In drug metabolism test on beagle dogs, the valsartan peaks in Examples 1 and 3 eluded faster than that of the comparative sample, indicating that Examples 1 and 3 may have become effective faster. In Examples 1, 3, and 5, valsartan, AHU377, and LBQ657 (the metabolite of AHU377) have significantly higher $C_{ma}$ and AUC than the comparative sample, indicating the Examples 1, 3, and 5 have better bioavailability. Accordingly, Examples 1, 3, and 5 may be better absorbed by the patient.

DETAILED DESCRIPTION

The present disclosure is explained in more details using the following examples. The examples herein illustrate the technical schemes and by no means limit the scope of the present disclosure. Any equivalents of the compounds or methods disclosed herein are within the scope of the current disclosure.

The HPLC spectra were obtained using Shimadzu LC-20A liquid chromatograph. The X-ray powder diffraction (XRPD) patterns were acquired using a Dandong Haoyuan DX-2700 X powder diffractometer. Its parameters are listed below.

|  | Reflection parameters |
| --- | --- |
| X ray reflection parameters | Cu, Kα |
|  | Kα1: 1.540598; Kα2: 1.544426 |
|  | Kα2/Kα1 intensity ratio: 0.50 |
| Voltage | 40 kV |
| Electric current | 30 mA |
| Divergence slit | Automatic |
| Scan Mode | Continuous |
| Scan range (2θ°) | 3.0 to 50.0 degrees |
| Sampling step (2θ°) | 0.02 degree |

Differential scanning calorimetry (DSC) data was acquired using a TAQ2000 differential scanning calorimeter, while thermal gravimetric analysis (TGA) data was measured using a TAQ5000 TGA instrument. Parameters of these instruments are listed below:

|  | DSC | TGA |
| --- | --- | --- |
| Sample Tray | aluminum plate, covered | platinum disc, open |
| Temperature | room temp. to 300° C. | room temp. to 350° C. |
| Scan rate | 10° C./min | 10° C./min |
| Protective gas | nitrogen | nitrogen |

Atomic absorption spectrophotometry (AAS) was used to determine the content of sodium of complexes in this disclosure. Instruments and materials used include: Puxi General TAS-990 atomic absorption spectrophotometer (Beijing Puxi General Instrument Co., Ltd.); standard sodium solution: 1000 μg/ml, GSB-04-1738-2004 (153050-2) National Non-Ferrous Metals and Electronic Materials Analysis Center. Experimental conditions include: a flame atomizer was used to atomize the sample; wavelength 589 nm; air pressure: 0.25 MPa; gas flow rate: 1300 ml/min; solvent: 0.1% KCl solution, linear range in the standard curve: 0.1 μg/ml-0.5 μg/ml, the concentration of the test solution: 4 μg/ml.

The calcium content in the complex was determined by EDTA complexometric titration. Materials used: EDTA titration solution (0.05 mol/L), calcium purpurin indicator, sodium hydroxide solution, 1 ml microburette. Methods: precisely weighing a sample of the complex (containing about 1.6 mg calcium), adding 50 ml water, then adding 50 ml sodium hydroxide solution to dissolve under ultrasound treatment, adding calcium purpurin 0.1 g, with EDTA titration solution (0.05 mol/L) titrating to the solution changing color from purple to pure blue. Blank experiments were conducted for calibration. One milliliter of the titration solution is the equivalent of 2 mg calcium. In this disclosure, "room temperature" means a temperature between 10-25° C.

EXAMPLE 1

Preparing [3-((1S, 3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate]$_6$CaNa$_{16}$.15H$_2$O AHU-377 (2.4 g, 5.83 mmol) and calcium salts of AHU-377 (1.26 g, 2.92 mmol) were added into 25 ml acetone and stirred for 30 min to obtain a clear solution. Valsartan (3.81 g, 8.75 mmol) was added to the clear solution and stirred until valsartan was completely dissolved.

A NaOH solution was prepared using NaOH (933 mg, 23.33 mmol) in water (2.7 mL). The NaOH solution added dropwise to the solution obtained above in less than 5 minutes in constant agitation. Solids started to precipitate within about 20-30 minutes. The solution was stirred continuously for more than 6 hours and then solids were separated through filtration. The solids was washed three times using acetone and then dried in air at room temperature. 7.4 g of the complex was obtained, representing a yield of 87.5%.

Using HPLC with external standards, the composition of the complex was calculated to include 45.35% valsartan and 42.86% AHU-377. The sodium content was 6.41%, obtained using atomic absorption spectrophotometry (AAS). The calcium content was 0.71%, obtained using EDTA complexometric titration. The water content was 4.66% as measured by Karl Fischer titration.

DSC of this crystalline sample showed characteristic adsorption peaks at about 120° C. and 151° C.

This crystalline sample was defined as a crystalline form of Complex I. Cu Kα radiation X-ray powder diffraction pattern of Complex I has diffraction angles, d-spacing and relative intensities of peaks listed in Table VII.

TABLE VII

| Peak No. | Pos. [°2θ] | d-spacing [Å] | Rel. Int. [%] |
| --- | --- | --- | --- |
| 1 | 4.12 | 21.43 | 100 |
| 2 | 5.11 | 17.29 | 32.58 |
| 3 | 5.57 | 15.87 | 15.90 |
| 4 | 12.43 | 7.12 | 27.08 |
| 5 | 15.20 | 5.83 | 5.96 |
| 6 | 16.89 | 5.25 | 10.46 |
| 7 | 17.71 | 5.00 | 7.13 |
| 8 | 18.62 | 4.77 | 7.27 |
| 9 | 19.96 | 4.45 | 6.50 |

The X-ray powder diffraction pattern of Complex I is shown in FIG. 1.

EXAMPLE 2

Preparing [3-((1S, 3R)-1-biphenyl-4-ylmethyl-3-ethoxycarbonyl-1-butylcarbamoyl)propionate-(S)-3'-methyl-2'-(pentanoyl {2"-(tetrazol-5-ylate)biphenyl-4'-ylmethyl}amino)butyrate]$_6$CaNa$_{16}$.15H$_2$O AHU-377 (2.41 g, 5.85 mmol) and calcium salt of AHU-377 (1.26 g, 2.93 mmol) were added into 25 ml acetone and stirred for 30 min to obtain a clear solution. Sodium salt of valsartan (4.21 g, 8.78 mmol) was added into the clear solution. The solution was stirred until the salt completely dissolved.

A NaOH solution was prepared with NaOH (234 mg, 5.85 mmol) in water (0.3 mL) and then added dropwise to the solution obtained above in less than 5 minutes and stirred constantly. Solids started to precipitate within 20-30 minutes. The solution was stirred continuously for more than 6 hours and then solids were separated by filtration. The solids were washed three times using acetone and then dried in air at room temperature. 6.8 g of the complex was obtained, representing a yield of 81.0%.

Using HPLC with external standards, the composition of the complex was calculated to include 45.30% valsartan and 42.89% AHU-377. The sodium content was 6.41%, obtained using atomic absorption spectrophotometry (AAS). The calcium content was 0.70%, obtained using EDTA complexometric titration. The water content was 4.70% as measured by Karl Fischer titration.

DSC of this crystalline sample showed characteristic adsorption peaks at about 121° C. and 152° C.

This crystalline sample has an X-ray powder diffraction pattern that is consistent with that of Example 1.

EXAMPLE 3

Preparing [3-((1S, 3R)-1-biphenyl-4-ylmethyl-3-ethoxycarbonyl-1-butylcarbamoyl)propionate-(S)-3'-methyl-2'-(pentanoyl {2"-(tetrazol-5-ylate)biphenyl-4'-ylmethyl}amino)butyrate]$_6$Ca$_2$Na$_{14}$.15H$_2$O AHU-377 (1.27 g, 3.08 mmol) and calcium salt AHU-377 (2.66 g, 6.17 mmol) were added into 25 ml acetone while stirring for 30 min to get a clear solution. Valsartan (4.03 g, 9.26 mmol) was added into the clear solution. The solution was stirred until valsartan completely dissolved.

A NaOH solution was prepared with NaOH (864 mg, 21.60 mmol) in water (0.9 mL) and added dropwise into the solution obtained above in less than 5 minutes during constant agitation. Solids started to precipitate within about 20-30 minutes. The solution was stirred for more than 6 hours and then the solids was separated by filtration. The solids was washed for three times using acetone and dried in air at room temperature. 7.4 g of the complex was obtained, representing a yield of 83.5%.

Using HPLC with external standards, the composition of the complex was calculated to include 45.47% valsartan and 43.03% AHU-377. The sodium content was 5.63%, obtained using atomic absorption spectrophotometry (AAS). The calcium content was 1.38%, obtained using EDTA complexometric titration. The water content was 4.76% as measured by Karl Fischer titration.

DSC of this crystalline sample showed characteristic adsorption peaks at about 125° C. and 155° C.

This crystalline sample was defined as a crystalline form of Complex II. Cu Kα radiation X-ray powder diffraction pattern of Complex II has diffraction angle, d-spacing and relative intensities of peaks listed in Table VIII.

TABLE VIII

| Peak No. | Pos. [°2θ] | d-spacing [Å] | Rel. Int. [%] |
| --- | --- | --- | --- |
| 1 | 4.05 | 21.81 | 100.00 |
| 2 | 5.07 | 17.42 | 30.51 |
| 3 | 5.54 | 15.94 | 13.11 |
| 4 | 9.91 | 8.93 | 1.85 |
| 5 | 12.31 | 7.19 | 27.24 |
| 6 | 15.03 | 5.89 | 4.51 |
| 7 | 16.85 | 5.26 | 6.57 |
| 8 | 17.81 | 4.98 | 4.33 |
| 9 | 19.85 | 4.47 | 2.94 |

The X-ray powder diffraction pattern of the crystalline sample is shown in FIG. 2.

EXAMPLE 4

Preparing [3-((1S, 3R)-1-biphenyl-4-ylmethyl-3-ethoxycarbonyl-1-butylcarbamoyl)propionate-(S)-3'-methyl-2'-(pentanoyl {2"-(tetrazol-5-ylate)biphenyl-4'-ylmethyl}amino)butyrate]$_6$Ca$_2$Na$_{14}$.15H$_2$O AHU-377 (1.27 g, 3.08 mmol) and calcium salt of AHU-377 (2.66 g, 6.17 mmol) were added into 25 ml acetone and stirred for 30 min to get a clear solution. Sodium salt of valsartan (4.44 g, 9.26 mmol) was added into the clear solution. The solution was stirred until the sodium salt completely dissolved.

A NaOH solution was prepared using NaOH (123 mg, 3.08 mmol) in water (0.15 mL) and added dropwise into the solution obtained above in less than 5 minutes under constant agitation. Solids started to precipitate within about 20-30 minutes. Stirring continued for more than 6 hours and then the solids were separated out by filtration, washed three times using acetone, and dried in air at room temperature. 7.2 g of the complex was obtained, representing a yield of 81.4%.

Using HPLC with external standards, the composition of the complex was calculated to include 45.33% valsartan and 42.95% AHU-377. The sodium content was 5.64%, obtained using atomic absorption spectrophotometry (AAS). The calcium content was 1.38%, obtained using EDTA complexometric titration. The water content was 4.77% as measured by Karl Fischer titration.

DSC of this crystalline sample showed characteristic adsorption peaks at about 123° C. and 154° C.

This crystalline sample has an x-ray powder diffraction pattern that is consistent with that of Example 3.

EXAMPLE 5

Preparing [3-((1S, 3R)-1-biphenyl-4-ylmethyl-3-ethoxycarbonyl-1-butylcarbamoyl)propionate-(S)-3'-methyl-2'-(pentanoyl {2"-(tetrazol-5-ylate)biphenyl-4'-ylmethyl}amino)butyrate]$_6$Ca$_3$Na$_{12}$.15H$_2$O Calcium salt of AHU-377 (2.66 g, 6.17 mmol) was dissolved in 25 ml acetone and stirred for 30 min to get a clear solution. Sodium salt of valsartan (2.96 g, 6.17 mmol) was added into the clear solution. The solution was stirred until the sodium salt completely dissolved. After stirring for 30-60 min at room temperature, white solids started to precipitate. Stirring continued for more than 8 hours and then the solids were filtered out, washed three times using acetone, dried in air at room temperature. 4.6 g of the complex was obtained, representing a yield of 78.0%.

Using HPLC with external standards, the composition of the complex was calculated to include 45.61% valsartan and 43.01% AHU-377. The sodium content was 4.76%, obtained using atomic absorption spectrophotometry (AAS). The calcium content was 2.06%, obtained using EDTA complexometric titration. The water content was 4.65% as measured by Karl Fischer titration.

DSC of this crystalline sample showed characteristic adsorption peaks at about 117° C. and 153° C.

The sample was defined as crystalline form of Complex III. Its Cu Kα radiation X-ray diffraction pattern has diffraction angles, d-spacing, and relative intensities as shown in Table IX.

TABLE IX

| Peak No. | Pos. [°2θ] | d-spacing [Å] | Rel. Int. [%] |
|---|---|---|---|
| 1 | 4.06 | 21.78 | 100.00 |
| 2 | 5.03 | 17.39 | 60.81 |
| 3 | 5.52 | 16.02 | 26.11 |
| 4 | 8.59 | 10.29 | 5.01 |
| 5 | 9.81 | 9.01 | 4.08 |
| 6 | 12.33 | 7.18 | 24.95 |
| 7 | 15.22 | 5.82 | 7.45 |
| 8 | 16.87 | 5.26 | 11.75 |
| 9 | 17.83 | 4.97 | 7.78 |

The X-ray powder diffraction pattern of this crystalline sample is shown in FIG. 3.

EXAMPLE 6

Preparing [3-((1S, 3R)-1-biphenyl-4-ylmethyl-3-ethoxycarbonyl-1-butylcarbamoyl)propionate-(S)-3'-methyl-2'-(pentanoyl {2''-(tetrazol-5-ylate)biphenyl-4'-ylmethyl}amino)butyrate]$_6$Ca$_3$Na$_{12}$.15H$_2$O Calcium salt of AHU-377 (2.66 g, 6.17 mmol) was added into 25 ml acetone and stirred for 20 min to get a clear solution. Valsartan (2.69 g, 6.17 mmol) was added into the clear solution. The solution was stirred until valsartan completely dissolved.

A NaOH solution was prepared with NaOH (494 mg, 12.34 mmol) in water (0.5 mL) and added dropwise into the solution obtained above in less than 5 minutes. After stirring at room temperature for 30-60 min, white solids started to precipitate. Stirring continued for more than 8 hours and was separated from the solution by filtration, washed three times using acetone, and dried in air at room temperature. 4.8 g of the complex was obtained, representing a yield of 81.5%.

Using HPLC with external standards, the composition of the complex was calculated to include 45.57% valsartan and 42.93% AHU-377. The sodium content was 4.84%, obtained using atomic absorption spectrophotometry (AAS). The calcium content was 2.13%, obtained using EDTA complexometric titration. The water content was 4.72% as measured by Karl Fischer titration.

DSC of this crystalline sample shows characteristic adsorption peaks at about 119° C. and 154° C.

The X-ray powder diffraction pattern of this crystalline sample is consistent with that of Example 5.

PREPARATION OF COMPARATIVE EXAMPLE LCZ696

Comparative Example LCZ696 was prepared according to Embodiment 1 in ZL200680001733.0, paragraphs [282]-[285].

Experiment 1

Chemical Stability Test

Inventive Examples 1, 2, 3, 4, 5, 6 and the comparative example were placed in their respective petri dishes to study their stability under high temperature (60° C.), high humidity (25° C., RH90%±5%), or strong light (4500 lux±500 lux). On Day 5 and Day 10, respectively, test samples were taken to test their purity. The test results are shown Table X below.

TABLE X

Purity Results in Stability Test

| Sample No. | Time (days) | Light 4500Lux | | Temperature 60° C. | | Humidity 25° C. RH90% | |
|---|---|---|---|---|---|---|---|
| | | Valsartan | AHU377 | Valsartan | AHU377 | Valsartan | AHU377 |
| Example 1 | 0 | 37.11 | 62.89 | 37.11 | 62.89 | 37.11 | 62.89 |
| | 5 | 37.13 | 62.85 | 37.09 | 62.87 | 37.12 | 62.84 |
| | 10 | 37.09 | 62.81 | 37.07 | 62.84 | 37.10 | 62.83 |
| Example 2 | 0 | 37.12 | 62.88 | 37.12 | 62.88 | 37.12 | 62.88 |
| | 5 | 37.11 | 62.84 | 37.11 | 62.89 | 37.11 | 62.86 |
| | 10 | 37.08 | 62.80 | 37.06 | 62.77 | 37.08 | 62.82 |
| Example 3 | 0 | 37.13 | 62.87 | 37.13 | 62.87 | 37.13 | 62.87 |
| | 5 | 37.09 | 62.84 | 37.11 | 62.81 | 37.12 | 62.82 |
| | 10 | 37.07 | 62.82 | 37.08 | 62.77 | 37.08 | 62.77 |
| Example 4 | 0 | 37.11 | 62.89 | 37.11 | 62.89 | 37.11 | 62.89 |
| | 5 | 37.08 | 62.86 | 37.07 | 62.82 | 37.10 | 62.87 |
| | 10 | 37.05 | 62.81 | 37.01 | 66.79 | 37.08 | 62.84 |
| Example 5 | 0 | 37.08 | 62.92 | 37.08 | 62.92 | 37.08 | 62.92 |
| | 5 | 37.06 | 62.86 | 37.04 | 62.83 | 36.99 | 62.86 |
| | 10 | 36.98 | 62.79 | 36.97 | 62.72 | 37.01 | 62.82 |
| Example 6 | 0 | 37.10 | 62.90 | 37.10 | 62.90 | 37.10 | 62.90 |
| | 5 | 37.04 | 62.81 | 37.01 | 62.82 | 37.03 | 62.83 |
| | 10 | 36.96 | 62.73 | 36.95 | 62.77 | 36.96 | 62.78 |

TABLE X-continued

Purity Results in Stability Test

| Sample No. | Time (days) | Light 4500Lux | | Temperature 60° C. | | Humidity 25° C. RH90% | |
|---|---|---|---|---|---|---|---|
| | | Valsartan | AHU377 | Valsartan | AHU377 | Valsartan | AHU377 |
| Comparative Example | 0 | 37.09 | 62.91 | 37.09 | 62.91 | 37.09 | 62.91 |
| | 5 | 37.04 | 62.84 | 37.03 | 62.81 | 37.05 | 62.89 |
| | 10 | 36.99 | 62.81 | 36.98 | 62.76 | 37.01 | 62.91 |

Results from the stability test show that, after exposure for 10 days to high temperature (60° C.), high humidity (25° C., RH90%±5%), or strong light (4500 lux±500 lux), inventive examples 1, 2, 3, 4, 5, 6 as well as the comparative example exhibited only slight decreases in purities determined using HPLC, indicating that all these crystalline complexes have good stability.

Experiment 2

Equilibrium Solubility Test

In order to investigate the solubility of inventive examples 1, 2, 3, 4, 5, 6 and the comparative example, their solubility were tested at 37° C. in a pH=1.0 (0.1 mol/L) hydrochloric acid, in a pH=3.5 ammonium acetate/ammonia buffer solution, and in a pH=6.8 potassium dihydrogen phosphate-sodium hydroxide buffer solution and water, respectively. The results are shown in Table XI below:

TABLE XI

Equilibrium Solubility Test Results

| Sample | pH 1.0 (mg/mL) | pH 3.5 (mg/mL) | pH 6.8 (mg/mL) | Water (mg/mL) |
|---|---|---|---|---|
| Example 1 | 0.07 | 0.49 | 16.00 | 5.78 |
| Example 2 | 0.06 | 0.51 | 16.10 | 5.75 |
| Example 3 | 0.06 | 0.48 | 16.42 | 4.73 |
| Example 4 | 0.07 | 0.49 | 16.45 | 4.68 |
| Example 5 | 0.07 | 0.46 | 16.20 | 3.77 |
| Example 6 | 0.07 | 0.45 | 16.23 | 3.74 |
| Comparative Example | 0.05 | 0.50 | >50 | >25 |

Test results show that the solubility of the inventive examples in the pH 3.5 buffer solution or the pH 1.0 hydrochloric acid is similar to but not as high as that of the comparative example.

Experiment 3

Hygroscopy Test

Inventive examples 1, 2, 3, 4, 5, 6 and the comparative example were placed flat in a clean, open weighing bottle at 25±1° C. under RH 80%±2% for 24 hours to assess the weight increase due to water absorption. The results are in Table XII.

TABLE XII

Hygroscopy Test Results

| Samples | Weight Increase | Appearance at Hour Zero | Appearance at Hour Twenty-Four |
|---|---|---|---|
| Example 1 | 6.95% | Off white powder | Off white powder |
| Example 2 | 6.98% | Off white powder | Off White powder |
| Example 3 | 4.55% | Off white powder | Off white powder |
| Example 4 | 4.51% | Off white powder | Off white powder |
| Example 5 | 2.12% | Off white powder | Off white powder |
| Example 6 | 2.09% | Off white powder | Off white powder |
| Comparative Example | 22.34% | Off white powder | Almost a liquid |

Hygroscopy test results above show that after 24 hours in high humidity, all of the inventive examples 1-6 had a weight increase of less than 7%. Example 6 only had a 2.09% weight increase and maintained its appearance. In contrast, the comparative example had a weight increase of more than 15% due to water absorption and almost became a liquid after 24 hours. This result shows that the comparative example was highly hygroscopic and would require more stringent conditions in downstream processing and storage. Because of this, relative to the comparative example, the inventive examples can be processed and stored under regular, less demanding conditions.

Experiment 4 in vivo Pharmacokinetic Studies in Beagle Dogs

1. Objectives

To discover, after one single dose via oral administration of the same molar dosage of Inventive Examples 1, 3, 5, and Comparative Example, the concentrations of valsartan, AHU377 and the metabolite of AHU377-LBQ657, as well as the basic pharmacokinetic characteristics, and compare the main parameters, including $C_{max}$, $T_{max}$, $AUC_{last}$, etc.

2. Materials and Methods 2.1 Medications being Tested

Example 1 in capsules: the capsules containing Example 1, provided by the Department of Drug Formulations of Chengdu Eastern Pharma Co., dosage 312 μmol/capsule, Lot: 150901;

Example 3 in capsules: the capsules containing Example 3, provided by the Department of Drug Formulations of Chengdu Eastern Pharma Co., dosage 312 μmol/capsule, Lot: 150901;

Example 5 in capsules: the capsules containing Example 5, provided by the Department of Drug Formulations of Chengdu Eastern Pharma Co., dosage 312 μmol/capsule, Lot: 150901;

Comparative Example LCZ696 in capsules: LCZ696 in capsules, provided by the Department of Drug Formulations of Chengdu Eastern Pharma Co., dosage 312 μmol/capsule, Lot: 150831;

2.2 Subject of Experiments

Four male Beagle dogs, body weight 8±2 kg, age 10-12 months, purchased from Chengdu Dashuo Biological Technology Co., Ltd., Certificate of Conformity: SCXK (Sichuan) 2013-24.

2.3 Experiment Design

The drug administration period: using Beagle dogs in a 4×4 crossover pilot study. There is a total of 4 test cycles. In each cycle 4 dogs were administered 4 different drug capsules. After each cycle, paused for two days to let the medications fully metabolize before starting the next experiment cycle. The details are shown in Table XIII below.

TABLE XIII

Beagle Dog Pharmacokinetics Study

| Animal ID | Tested drugs | | | |
|---|---|---|---|---|
| | Cycle 1 | Cycle 2 | Cycle 3 | Cycle 4 |
| MD1 | Comparative Example | Example 1 | Example 3 | Example 5 |
| MD2 | Example 1 | Comparative Example | Example 5 | Example 3 |
| MD3 | Example 3 | Example 5 | Comparative Example | Example 1 |
| MD4 | Example 5 | Example 3 | Example 1 | Comparative Example |

Note:
the MD = Male Dog.

2.4 Sample Collection

In every cycle, 1 ml blood sample was collected in EDTA-K2 tubes at 5 min, 15 min, 0.5 h, 1 h, 2 h, 3 h, 4 h, 6 h, 8 h, 10 h, 24 h, 36 h, 48 h prior to and after administering the single dosage into the forelimb or hind limb veins and centrifuged for 10 min at 3000 r/min. Plasma was separated and kept in a freezer at −70° C.

2.5 LC/MS/MS Biological Sample Analysis

Evenly mixing 50 µl plasma with 5 µl of a working solution or a blank diluent, adding 150 µl precipitating agent acetonitrile that contains an internal standard, vortex mixed for 2 minutes, centrifuged for 5 minutes at 12000 rpm. 100 µl supernatant was mixed with 100 µl pure water. The injection sample size was 10 µl.

2.6 Statistical Methods

SPSS was used for statistical analysis and experimental data was expressed with the mean plus or minus standard deviation. Comparison between the multiple sets of data used analysis of variance (ANOVA), while Least Significant Difference (LSD) Test was employed to compare two data points.

2.7 Experimental Results

TABLE XIV

Pharmacokinetics parameters obtained in the study

| Treatment Programs | $T_{MAX}$, h | $C_{MAX}$, ng/mL | $AUC_{0-Last}$, ng * h/mL |
|---|---|---|---|
| Valsartan | | | |
| Example 1 Capsule | 0.56 ± 0.31* | 6765 ± 1724* | 23166 ± 3467* |
| Example 3 Capsule | 0.75 ± 0.29 | 7034 ± 1672* | 24784 ± 4979* |
| Example 5 Capsule | 2.00 ± 1.40 | 6584 ± 1533* | 21713 ± 1667* |
| Compara. Exp. Capsule | 2.25 ± 1.25 | 3937 ± 1748 | 17628 ± 2834 |

TABLE XIV-continued

Pharmacokinetics parameters obtained in the study

| Treatment Programs | $T_{MAX}$, h | $C_{MAX}$, ng/mL | $AUC_{0-Last}$, ng * h/mL |
|---|---|---|---|
| AHU377 | | | |
| Example 1 Capsule | 0.56 ± 0.31 | 1278 ± 222* | 2499 ± 320* |
| Example 3 Capsule | 0.63 ± 0.25 | 1377 ± 331* | 2541 ± 383* |
| Example 5 Capsule | 0.44 ± 0.12 | 1320 ± 285* | 3249 ± 603* |
| Compara. Exp. Capsule | 0.63 ± 0.25 | 758 ± 352 | 1829 ± 415 |
| LBQ657 | | | |
| Example 1 Capsule | 1.13 ± 0.63 | 1486 ± 346* | 5693 ± 548* |
| Example 3 Capsule | 1.50 ± 0.58 | 1474 ± 362* | 5818 ± 722* |
| Example 5 Capsule | 1.75 ± 0.50 | 1574 ± 421* | 5899 ± 796* |
| Compara. Exp. Capsule | 1.63 ± 0.75 | 869 ± 334 | 4579 ± 698 |

"*P": compared with the comparative example, P < 0.05;

After a single oral administration of the drug capsule, $T_{MAX}$ of valsartan for Examples 1 and 3 moved significantly earlier. Especially, $T_{MAX}$ of valsartan for Example 1 showed statistical significance in comparison with the comparative example (*P<0.05). In Examples 1, 3, and 5, valsartan, AHU377, and LBQ657 (the metabolite of AHU377) showed $C_{MAX}$ and AUC values clearly higher than that of the comparative sample (*P<0.05), providing evidence that valsartan and AHU377 have been absorbed better than the comparative example by the beagle dogs.

CONCLUSION

The metabolism tests in Beagle dogs show that Examples 1 and 3 arrived at peak value in valsartan faster than the comparative examples did, indicating that Examples 1 and 3 become effective fasters. Examples 1, 3, and 5 clearly exhibited higher $C_{max}$ and AUC in valsartan, AHU377, and LBQ657 (the metabolite of AHU377) than that of the comparative example, indicating a higher bioavailability. That is, under the conditions of this set of experiments, Examples 1, 3, and 5 demonstrated better absorptions than the comparative example did.

According to the above results, the inventive examples disclosed herein have better bioavailability and can be more effective in the prevention of heart failure. Those of ordinary skill in the art may modify or vary the complex, the crystalline form, and the method of making in a variety of ways without departing from the spirit or scope of the present invention, as long as the modifications or variations are within the scope of the claims and equivalents thereof.

What is claimed is:

1. A complex of sodium calcium [3-((1S, 3R)-1-biphenyl-4-ylmethyl-3-ethoxy carbonyl-1-butylcarbamoyl)propionate-(S)-3'-methyl-2'-(pentanoyl {2"-(tetrazol-5-ylate)biphenyl4'-ylmethyl}amino)butyrate].

2. The complex of claim 1 having a formula of [3-((1S, 3R)-1-biphenyl-4-ylmethyl-3-ethoxycarbonyl-1-butylcarbamoyl)propionate-(S)-3'-methyl -2'-(pentanoyl{2"-(tetrazol-5-ylate) biphenyl-4'-ylmethyl}amino) butyrate]$_6$•X$Ca^{2+}$•YNa$^+$•Z$H_2O$, wherein X=1-3, Y=12-16, Z=9-18, and 2X+Y=18, and represented by ·XCa²⁺·YNa⁺·ZH₂O.

3. The complex of claim 2, wherein X=1, Y=16, Z=12-18.

4. The complex of claim 2, wherein X=1, Y=16, Z=12, 15 or 18.

5. The complex of claim 2, wherein X=2, Y=14, and Z=9-15.

6. The complex of claim 5, wherein X=2, Y=14, Z=12, 15 or 9.

7. The complex of claim 2, wherein X=3, Y=12, and Z=9-15.

8. The complex of claim 2, wherein X=3, Y=12, Z=12, 15 or 9.

9. The complex of claim 1, in crystalline form.

10. The complex of claim 4, in crystalline form, wherein X=1, Y=16, Z=15, having an x-ray powder diffraction pattern with diffraction angle, d-spacing and relative intensity of peak listed in the following table:

| Peak No. | Pos. [°2θ]* | d-spacing [Å] | Rel. Int. [%] |
| --- | --- | --- | --- |
| 1 | 4.12 | 21.43 | 100.00 |
| 2 | 5.11 | 17.29 | 32.58 |
| 3 | 5.57 | 15.87 | 15.90 |
| 4 | 12.43 | 7.12 | 27.08 |
| 5 | 15.20 | 5.83 | 5.96 |
| 6 | 16.89 | 5.25 | 10.46 |
| 7 | 17.71 | 5.00 | 7.13 |
| 8 | 18.62 | 4.77 | 7.27 |
| 9 | 19.96 | 4.45 | 6.50 | wherein the diffraction angle has a margin of error of ±0.2.

11. The complex of claim 10 having an x-ray powder diffraction pattern substantially as shown in FIG. 1.

12. The complex of claim 6 in crystalline form, wherein X=2, Y=14, Z=15, having an x-ray powder diffraction pattern with diffraction angle, d-spacing and relative intensity of peak listed in the following table:

| Peak No. | Pos. [°2θ]* | d-spacing [Å] | Rel. Int. [%] |
| --- | --- | --- | --- |
| 1 | 4.05 | 21.81 | 100.00 |
| 2 | 5.07 | 17.42 | 30.51 |
| 3 | 5.54 | 15.94 | 13.11 |
| 4 | 9.91 | 8.93 | 1.85 |
| 5 | 12.31 | 7.19 | 27.24 |
| 6 | 15.03 | 5.89 | 4.51 |
| 7 | 16.85 | 5.26 | 6.57 |
| 8 | 17.81 | 4.98 | 4.33 |
| 9 | 19.85 | 4.47 | 2.94 | wherein the diffraction angle has a margin of error of ±0.2.

13. The complex according to claim 12 having an x-ray powder diffraction pattern substantially as shown in FIG. 2.

14. The complex of claim 8 in crystalline form, wherein X=3, Y=12, Z=15, having an x-ray powder diffraction pattern with diffraction angle, d-spacing and relative intensity of peak listed in the following table:

| Peak No. | Pos. [°2θ]* | d-spacing [Å] | Rel. Int. [%] |
| --- | --- | --- | --- |
| 1 | 4.06 | 21.78 | 100.00 |
| 2 | 5.03 | 17.39 | 60.81 |
| 3 | 5.52 | 16.02 | 26.11 |
| 4 | 8.59 | 10.29 | 5.01 |
| 5 | 9.81 | 9.01 | 4.08 |
| 6 | 12.33 | 7.18 | 24.95 |
| 7 | 15.22 | 5.82 | 7.45 |
| 8 | 16.87 | 5.26 | 11.75 |
| 9 | 17.83 | 4.97 | 7.78 | wherein the diffraction angle has a margin of error of ±0.2.

15. The complex according to claim 14 having an x-ray powder diffraction pattern substantially as shown in FIG. 3.

16. A method for preparing the complex of claim 1, comprising the following steps:
dissolving AHU-377 and/or a calcium salt thereof in acetone to form a first solution;
dissolving valsartan and/or its sodium salt in the first solution to form a second solution;

adding a NaOH solution into the second solution;
forming to a solid precipitant in the second solution under constant stirring;
separating the solid from the second solution;
washing the solid with acetone; and
drying the solid in ambient air to obtain the complex.

17. The method of claim 16, wherein a molar ratio of $Ca^{2+}:Na^+$ in the second solution after the addition of NaOH ranges from 1:16 to 6:6.

18. The method of claim 17, wherein the molar ratio of $Ca^{2+}:Na^+$ ranges from 1:16 to 3:12.

19. A method of treating chronic heart failure, comprising administering an effective amount of medicament containing the complex of claim 1 to a patient in need thereof.

* * * * *